(12) United States Patent  (10) Patent No.: US 8,517,731 B2
Mosimann  (45) Date of Patent: Aug. 27, 2013

(54) PIPE AND UNIVERSAL COUPLING FOR SUPPLYING INSTRUMENTS FOR DENTAL OR SURGICAL USE

(75) Inventor: Vincent Mosimann, La Neuveville (CH)

(73) Assignee: Bien-Air Holding SA, Bienne (CH)

( * ) Notice: Subject to any disclaimer, the term of this patent is extended or adjusted under 35 U.S.C. 154(b) by 893 days.

(21) Appl. No.: 11/568,867

(22) PCT Filed: May 9, 2005

(86) PCT No.: PCT/EP2005/004987
§ 371 (c)(1),
(2), (4) Date: Nov. 9, 2006

(87) PCT Pub. No.: WO2005/115264
PCT Pub. Date: Dec. 8, 2005

(65) Prior Publication Data
US 2007/0248934 A1 Oct. 25, 2007

(30) Foreign Application Priority Data
May 28, 2004 (EP) .................................. 04012687

(51) Int. Cl.
*A61C 1/08* (2006.01)
(52) U.S. Cl.
USPC ....................................................... 433/126
(58) Field of Classification Search
USPC ............. 433/80, 82, 119, 126; 604/533–539; 285/52, 124.1, 258
See application file for complete search history.

(56) References Cited

U.S. PATENT DOCUMENTS

| 1,890,290 | A |   | 12/1932 | Hargreaves |
| 3,295,514 | A | * | 1/1967 | Hein et al. ....................... 433/81 |
| 4,080,737 | A |   | 3/1978 | Fleer |
| 2001/0031442 | A1 |   | 10/2001 | Mosimann |
| 2003/0073055 | A1 | * | 4/2003 | Pollock et al. ................ 433/126 |
| 2003/0092324 | A1 |   | 5/2003 | Walker et al. |

FOREIGN PATENT DOCUMENTS

| CH | 676081 A5 | 12/1990 |
| EP | 0 745 358 A1 | 12/1996 |
| EP | 1 310 721 A2 | 5/2003 |

OTHER PUBLICATIONS

International Search Report issued in corresponding application No. PCT/EP2005/004987 completed Jul. 26, 2005 and mailed Aug. 4, 2005.

* cited by examiner

*Primary Examiner* — Robyn Doan
*Assistant Examiner* — Matthew Nelson
(74) *Attorney, Agent, or Firm* — Griffin & Szipl, P.C.

(57) ABSTRACT

A supply pipe for connecting an instrument for dental or surgical use to a control and supply unit contains fluid conduits and electric lines and includes at a front end a universal coupling for connecting different types of the instrument in a removable manner to part or all of the conduits and lines. The universal coupling includes fluid connectors coupled to conduits and electric connectors coupled to lines, wherein each of the connectors occupies a place on a front face of the universal coupling. The supply pipe contains at least one additional electric line including an additional conductor which is not coupled to one of the electric connectors, but to one of the fluid connectors of the universal coupling, wherein the dual function connector is arranged to provide a choice between a fluid connection, an electric connection or both.

19 Claims, 5 Drawing Sheets

PIPE AND UNIVERSAL COUPLING FOR SUPPLYING INSTRUMENTS FOR DENTAL OR SURGICAL USE

This is a National Phase Application in the United States of International Patent Application No. PCT/EP2005/004987 filed May 9, 2005, which claims priority on European Patent Application No. 04012687.2, filed May 28, 2004. The entire disclosures of the above patent applications are hereby incorporated by reference.

FIELD OF THE INVENTION

The present invention concerns a supply pipe for connecting an instrument for dental or surgical use to a control and supply unit, wherein the pipe contains fluid conduits and electrical lines and comprises at a front end a universal coupling for connecting different types of the instrument to a part of or to all of the conduits and lines in a removable manner, the universal coupling comprising fluid connectors coupled to the conduits and electrical connectors connected to the lines, each of the connectors occupying a place on a front face of the universal coupling.

BACKGROUND OF THE INVENTION

Pipes and adapters of this type are well known and are described in particular in Patent Application Nos. CH 676 081 and EP 745 358 by the same Applicant, the back end of the supply pipe being connected to a supply and control unit that can deliver, via the pipe, various fluids and various currents or electrical signals for actuating and/or controlling various apparatus or instruments able to be connected as required to the front end of the pipe. For this purpose, the front end is provided with a universal coupling that is also called an "attachment". The latter generally contains several fluid connectors and several electrical connectors. Depending upon the type and nature of the instrument that has to be coupled, all of the connectors of the coupling or only certain of them will be used and will thus be coupled to corresponding connectors of the instrument or of an intermediate coupling, as is explained particularly in EP Patent Application No. 745 358. This is why the coupling or attachment is termed universal. Similar couplings, having a different arrangement of the connectors are disclosed in U.S. Pat. No. 4,080,737.

Figure 1:
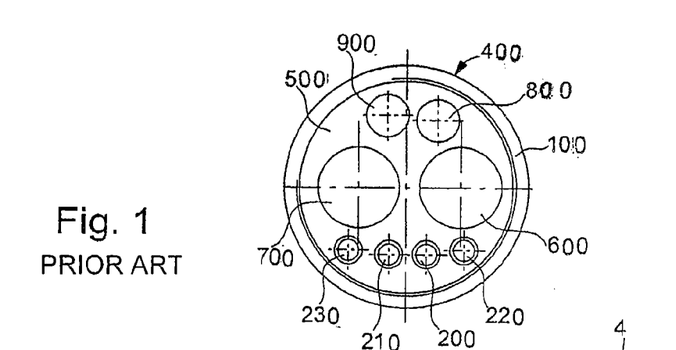
FIG. 1 shows the front face of a known supply pipe coupling for dental instruments, such as disclosed by CH Patent No. 676 081.

FIG. 2 of CH Patent No. 676 081 shows the front face of the universal coupling or attachment 400, which is fitted to the front end of the supply pipe. FIG. 1 of this paper corresponds to FIG. 2 of CH Patent No. 676 081, Coupling 400 comprises a body 500 made of insulating material carrying a rotating threaded sleeve 100 that enables coupling 400 to be fixed to the associated couplings in a removable manner. Body 500 contains four connectors 600, 700, 800 and 900 for fluids and four electric connectors 200, 210, 220 and 230, which are arranged in a standarized manner so that they can be used with instruments from different manufacturers. In the example described here, which refers to the products marketed under the name 4VLM by Bien-Air Dental SA, Bienne, Switzerland, connector 600 is associated with a conduit which brings pressurized air to the turbine of a handpiece, whereas connector 700 is associated with a return conduit for the air. Connector 800 is associated with a conduit which brings water to the instrument, whereas connector 900 is associated with a conduit that supplies pulsed air to the instrument, wherein the water and pulsed air are for cleaning, drying or cooling the work area. The pair of electric connectors 200 and 210 is for an electric circuit powering a lamp for illuminating the work area. The pair of electrical connectors 220 and 230 is used for the circuit powering an electric motor for a handpiece or for an electric device of a different type from a motor or a lamp, for example, an ultrasound scaling apparatus. Using the supply circuit passing through connectors 220 and 230 is also known for transmitting electric control or measurement signals, in the form of encoded pulses.

The front face arrangement shown in FIG. 2 of CH Patent No. 676 081 has been very widely used in the world for many years, particularly because of its versatility and the standardization of the couplings supplied by the main manufacturers. However, this standardization has a drawback in certain cases, because it becomes almost impossible to install additional connectors in such a coupling, since virtually all of the available places on the front face are occupied by the usual connectors. With developments in technology and in particular in dental or surgical handpiece, additional or different connections between the hand piece and the control and supply unit have become desirable or necessary, and it would be useful to make them without having to alter most of the couplings of the instruments that practitioners are currently using. A typical example of such an additional connection is the earthing (grounding) of certain apparatus or instruments whose electric circuits could pose a risk for a patient. Earthing, which is compulsory in certain cases, would mean using one of the four connectors 200 to 230 in the example of FIG. 1 (FIG. 2 of CH Patent No. 676 081), and could thus lead to removal of one of the electric circuits. There, therefore, exists a requirement for another solution to this problem.

In other technical fields, conductive circuits have been incorporated in fluid pipes and in their connectors in order to form an earth line. For example, in order to dissipate any electrostatic charges, a solution shown in FIGS. 6 to 8 of EP Patent Application No. 1 310 721 uses pipes having a conductive layer and connectors having contact parts located inside the fluid conduit.

Another example is found in U.S. Pat. No. 1,890,290, which discloses couplings for fire hose pipes whose walls contain a pair of conductive wires forming an electric signal transmission circuit. The connection of one of the wires is carried out directly by the threaded metal rings of the couplings, whereas the connection of the second wire is carried out via contact parts arranged in the fluid conduit. This arrangement appears to be difficult to use reliably, if one considers that at least one of the two electric lines would have to be well insulated over its entire length with respect to the external medium and the water contained in the pipe.

SUMMARY OF THE INVENTION

The present invention concerns an arrangement of a supply pipe, in particular of its universal coupling, which increases the number of electrical connections in order to offer other possibilities of combining supply or control lines and conduits and which thus allows new types of dental or surgical instruments to be connected as required, without necessarily changing the usual arrangement of the connectors in the universal coupling or the dimensions of the latter.

There is therefore provided a supply pipe of the type stated in the above preamble, characterized in that it contains at least one additional electric line including an additional conductor which is not connected to one of the electric connectors, but to one of the fluid connectors of the universal coupling, this dual function connector being arranged to ensure a fluid connection, an electric connection or both, as required.

Thus, the invention not only actually increases the number of electric connections available while preserving the arrangement and size of the universal coupling, but it also multiplies the number of different arrangements of connectors in the couplings to be connected to the universal coupling, in particular the couplings belonging to the various instruments that one could envisage supplying via the pipe and the associated unit.

In a first embodiment, the dual function connector includes a tubular metal part electrically connected to the additional connector and connected to a flexible tube extending into the pipe, to form a fluid conduit with the pipe, the tubular part forming both an electric contact member and a fit member for cooperating with a tubular part of a connector forming part of a second coupling connected to the instrument. Owing to the invention, this second coupling, which will be coupled to the universal coupling in a removable manner, can have more varied configurations than in the prior art, since in order to cooperate with each dual function connector of the universal coupling, it can include either a fluid connector or an electric connector, or a dual function connector at the corresponding place.

In another embodiment, the dual function connector can include a cylindrical bore, arranged in an insulating body of the universal coupling, and a male, female or hermaphrodite contact, arranged at the centre of the cylindrical bore and electrically connected to the additional conductor.

Thus, in accordance with a third embodiment of the present invention, a supply pipe for connecting an instrument for dental or surgical use to a control and supply unit is provided, wherein the pipe contains fluid conduits and electric lines and includes, at a front end, a universal coupling (4) for connecting different types of the instrument in a removable manner to part or all of the conduits and lines, and the universal coupling includes fluid connectors (6 to 9) coupled to the conduits and electric connectors (20 to 23) coupled to the lines, wherein each of the connectors occupies a place on a front face (11) of the universal coupling, and the supply pipe (1) is characterized in that it contains at least one additional electric line including an additional conductor (24) which is not coupled to one of the electric connectors (20 to 23), but to one (7) of the fluid connectors of the universal coupling (4), and the dual function connector is arranged to provide a choice between a fluid connection, an electric connection or both.

In accordance with a fourth embodiment of the invention, the third embodiment is modified so that the dual function connector (7) includes a tubular metal part (30) electrically connected to the additional conductor (24) and coupled to a flexible tube (17) extending into the pipe, to form, with the tube, a fluid conduit (13), and the tubular part forms both an electric contact member and a fit member for cooperating with a tubular part (32) of a connector connected to the instrument. In accordance with a fifth embodiment of the invention, the fourth embodiment is further modified so that the additional conductor (24) is arranged in the fluid conduit (13) inside the tube (17). In accordance with a sixth embodiment of the present invention, the fifth embodiment is further modified so that the additional conductor (24) is coupled to a metal sleeve (25) secured to the tubular part (30) and located in the fluid conduit (13).

In accordance with a seventh embodiment of the invention, the fourth embodiment is modified so that the additional conductor (24) is arranged in the wall of the tube (17). In accordance with an eighth embodiment of the present invention, the fourth embodiment is modified so that the additional conductor (24) is arranged outside the tube (17). In accordance with a ninth embodiment of the invention, the third, fourth, fifth, sixth, seventh, and/or eighth embodiments are further modified so that the conduit associated with the dual function connector (7) is an air conduit (13). In accordance with a tenth embodiment of the present invention, the third embodiment is modified so that the dual function connector (7) includes a cylindrical bore (52) arranged in an insulating body (5) of the universal coupling (4), and a contact element (55) arranged at the center of the cylindrical bore and electrically connected to the additional conductor (24).

DETAILED DESCRIPTION OF VARIOUS EMBODIMENTS OF THE INVENTION

A first embodiment will be described by way of example with reference to FIG. 2, one part (a) of which shows a universal coupling 4 mounted at the front end of a supply pipe 1 from a supply and control unit, whereas part (b) shows schematically one part of a back coupling 2 arranged to be coupled with coupling 4. The back coupling 2 can form part of an intermediate part or a handpiece, or even another apparatus supplied and/or controlled via pipe 1, for example, an apparatus including an electric motor or an air turbine.

Figure 2:
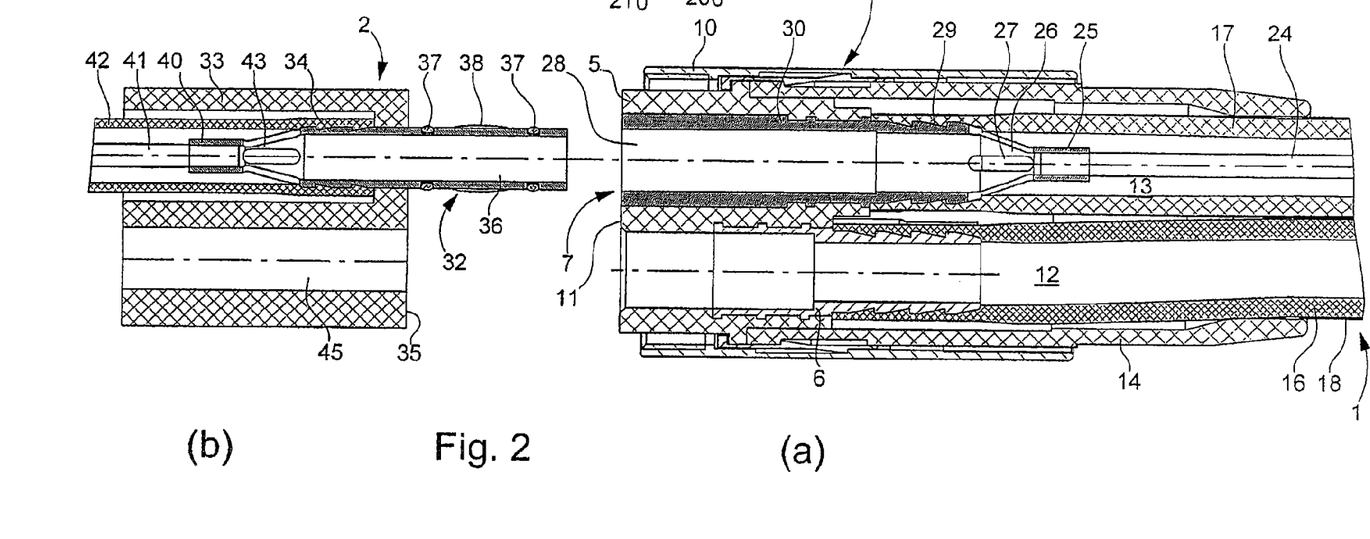
FIG. 2 shows in a schematic manner a first embodiment of the invention, part (a) of the Figure being a longitudinal cross-section of a female coupling mounted on the supply pipe, for example along line II-II of FIG. 6, while part (b) of the Figure is a longitudinal cross-section of a male coupling arranged for cooperating with the female coupling.
Figure 6:
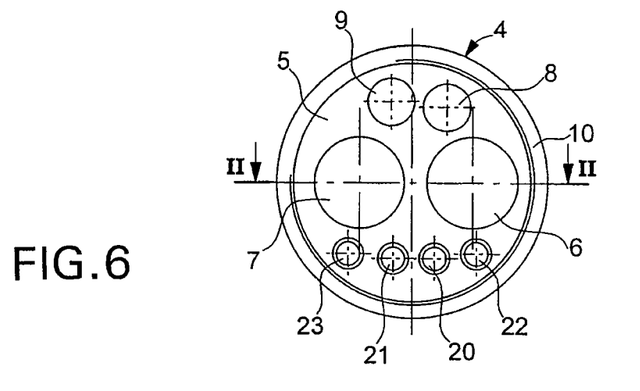
FIG. 6 shows the front face of the supply pipe coupling for dental instruments corresponding to the embodiment of FIG. 2.

Coupling 4 of FIGS. 2 and 6 of the present application is similar to that of FIG. 1 (FIG. 2 of CH Patent No. 676 081) described above, but altered in many ways by the addition of an additional electric line, in this case an earth line (i.e., a ground). FIGS. 2 and 6 of the present application show a body 5 made of insulating synthetic material, containing in particular the female connector 6 for a pressurized air conduit 12 and the female connector 7 for a return air conduit 13. Body 5 is mounted in a bushing 14 which carries rotating sleeve 10 and whose back end surrounds supply pipe 1. The latter includes four flexible tubes for fluids, namely a tube 16 fitted onto the back of connector 6, a tube 17 fitted onto the back of connector 7 and two other tubes connected to fluid connectors 8 and 9, and in addition four insulated electric lines respectively connected to electric connectors 20 to 23. Pipe 1 preferably includes a flexible sheath 18 covering all of the tubes and lines.

In supply pipe 1, a flexible conductor 24 that extends freely inside the return air tube 17, for example a non-insulated copper braid wire, forms the earth line. Of course, one could use an insulated conductor if the line in question were not an earth line or if the conduit that contains it could contain a conductive fluid. In the present case, we have chosen to place the earth line in tube 17 because it is the biggest, although the reduction of the air passage section is proportionally the smallest. Conductor 24 is mechanically and electrically connected, for example, by crimping and/or welding, to the back end of connector 7, which extends in the form of a small central sleeve inside air conduit 13. A conical part 26 provided with several orifices 27 for the passage of air connects sleeve 25 to the main tubular part 30 of connector 7, having a cylindrical bore 28, which opens onto the front face 11 of coupling 4. Connector 7 is evidently made of a good electrical conductive material, preferably a metal, and the external surface 29 of its tubular part 30 is fitted in an impervious manner into tube 17, such that it can be used at the same time or alternatively as air connector and/or electric connector, in a way that does not require an additional place on front face 11 of coupling 4.

Given that the earth line including conductor 24 and connector 7 are still at zero electric potential in relation to earth, its components do not need any electric insulation and can thus be in contact with the return air that passes in conduit 13 and which may be charged with water droplets sucked up over the work area. However, the earth line can evidently be combined with other tubes of pipe 1, including a tube carrying a conductive fluid such as water.

In this example, connector 6 of compressed air conduit 12 is made in a conventional manner, but it could of course be adapted to a dual pneumatic and electric function like connector 7, in combination with an electric control or supply line passing in tube 16 where the compressed air is dry, like conductor 24 in the other tube. One would thus have a new electric circuit comprising two lines in pipe 1. However, connector 6 would then have to be insulated.

In part (b) of FIG. 2, only those elements of coupling 2 that are peculiar to the implementation of the present invention are shown. In order to cooperate with female connector 7, a male connector 32 with a dual pneumatic and electric function is mounted in body 33 of the coupling and comprises a tubular part 34 which protrudes from the front face 35 of the body so that it can be plugged into bore 28 of connector 7 and its inner bore 36 can thus be connected to the return air conduit 13. In order to cooperate with the surface of bore 28, the external surface of part 34 is provided with O-ring sealing gaskets 36 and projecting portions 37 providing a good electric contact. The other end of connector 32, located on the side considered here to be the front, can be made in a similar manner to that of connector 7, with a small central bushing 40 fixed to the end of a conductor 41 extending into a tube 42 which conveys the return air from the connected instrument. A conical cut out portion 43 secures bushing 40 and tubular part 34 of the male connector, which is preferably made of metal.

In connector 7, the position of sleeve 25 and conical part 26 beyond the back end of tubular part 30 has two advantages. On the one hand, this allows sleeve 25 to be easily crimped or welded onto conductor 24, and on the other hand, elements 25 and 26 do not interfere with male connector 32 housed in tubular part 30. The latter is thus no longer than in the conventional embodiment according to FIG. 1, i.e. the invention does not require universal coupling 4 to be made longer.

Coupling 2 further comprises other male (or female or hermaphrodite depending upon the case) connectors for cooperating with all or part of the connectors of universal coupling 4, depending upon the requirements of the instrument coupled thereto. If, for example, female connector 6 had a dual pneumatic and electric function like connector 7, a corresponding male connector, similar to connector 32, could be mounted in a channel 45 of body 33.

In current dental instruments having a coupling of the same type as coupling 2, body 33 is generally metallic. It may also be so in the present example provided that the electric line passing through connector 32 is an earth line. However, body 33 would have to be made of insulating material if connector 32 or another similar connector arranged in coupling 2 formed part of an electric line with non-zero potential.

In light of the preceding description, it will easily be understood that depending upon the type of instrument to be supplied via pipe 1, dual function connector 7 can receive either a dual pneumatic and electric function connector, like connector 32, or a purely pneumatic connector as is the case in the prior art, or a purely electric connector, if the instrument being supplied does not need return air, for example a surgical instrument with an electric motor. Coupling 4 thus has increased versatility.

It will be noted that in most cases, the additional electric line passing through the dual function connector could be used, either for transmitting signals and/or electric power supply.

Figure 3:
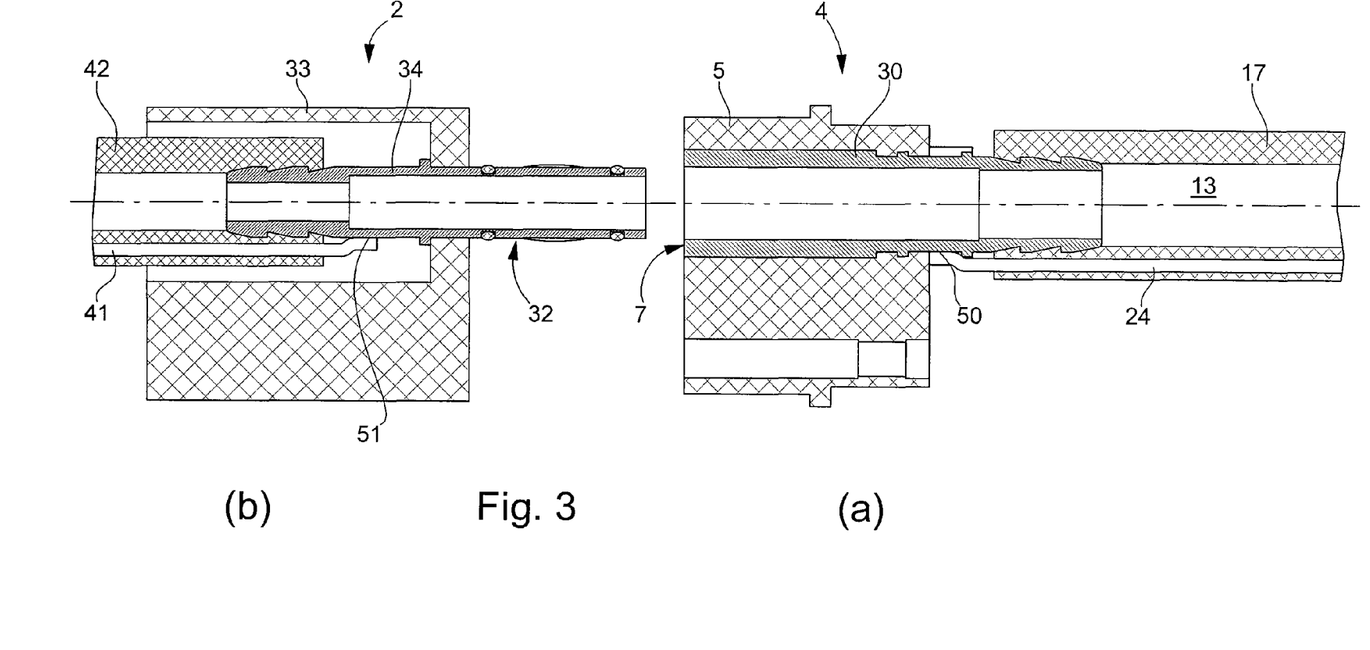
FIG. 3 shows in a schematic manner a second embodiment in the same application as FIG. 2 in a partial longitudinal cross-section showing a male coupling at (a) and a female coupling at (b).
Figure 4:
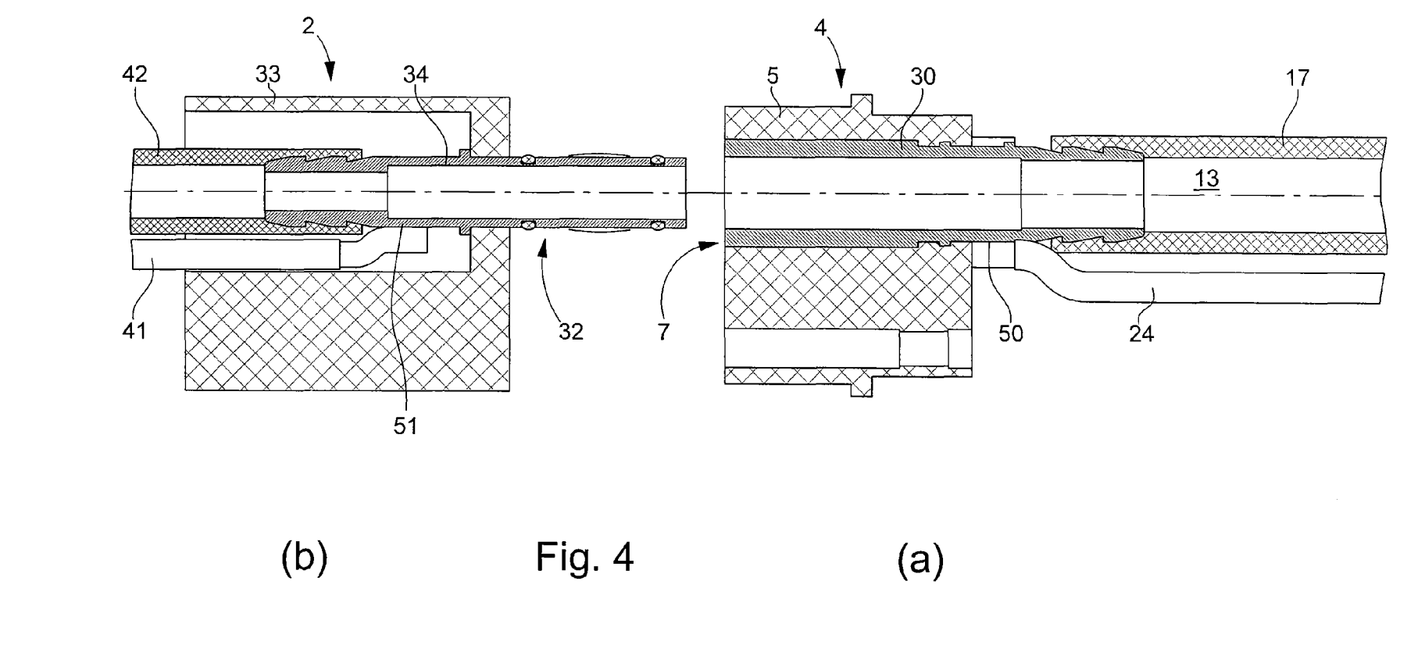
FIG. 4 is a view similar to FIG. 3 and shows in a schematic manner a third embodiment showing a female coupling at (a) and a male coupling at (b).

FIGS. 3 and 4 illustrate two other embodiments, which do not differ substantially from the first except for the location of the additional electric line in relation to the associated fluid conduit. This is why the drawings are simplified and only these differences will be described below.

In the embodiment of FIG. 3, conductors 24 and 41 are embedded in the thickness of the wall of the corresponding tubes 17 and 42 instead of being in air conduit 13. Their respective ends are welded at 50, 51 to the external surface of tubular part 30, 34 of the associated connector. This conductor can take the form of a flexible metal strip or a flattened braid and can be incorporated in the wall during manufacture of the tube via extrusion. It will be noted that conductors 24 and 41 are thereby sheltered from the fluids flowing in the supply pipe, which can prevent any corrosion problems. Moreover, they do not reduce the air passage section in conduit 13.

In the embodiment of FIG. 4, conductors 24 and 41 are placed outside the corresponding tubes 17 and 42 and they preferably have an insulating sheath. Their respective ends are stripped and welded at 50, 51 to the external surface of tubular part 30, 34 of the associated connector as in the example of FIG. 3. The insulated conductor 24 is housed in supply pipe 1 in the same manner as the usual electric conductors coupled to connectors 20 to 23, such that it can also be coupled in the same manner as the latter to the supply and control unit.

It will be noted that any of the male connectors 32 of FIGS. 2b, 3b and 4b can be plugged in to any of the female connectors 7 of FIGS. 2a, 3a and 4a. In other words, the arrangement of the additional conductor does not need to be the same in the two coupled couplings 2 and 4.

Figure 5:
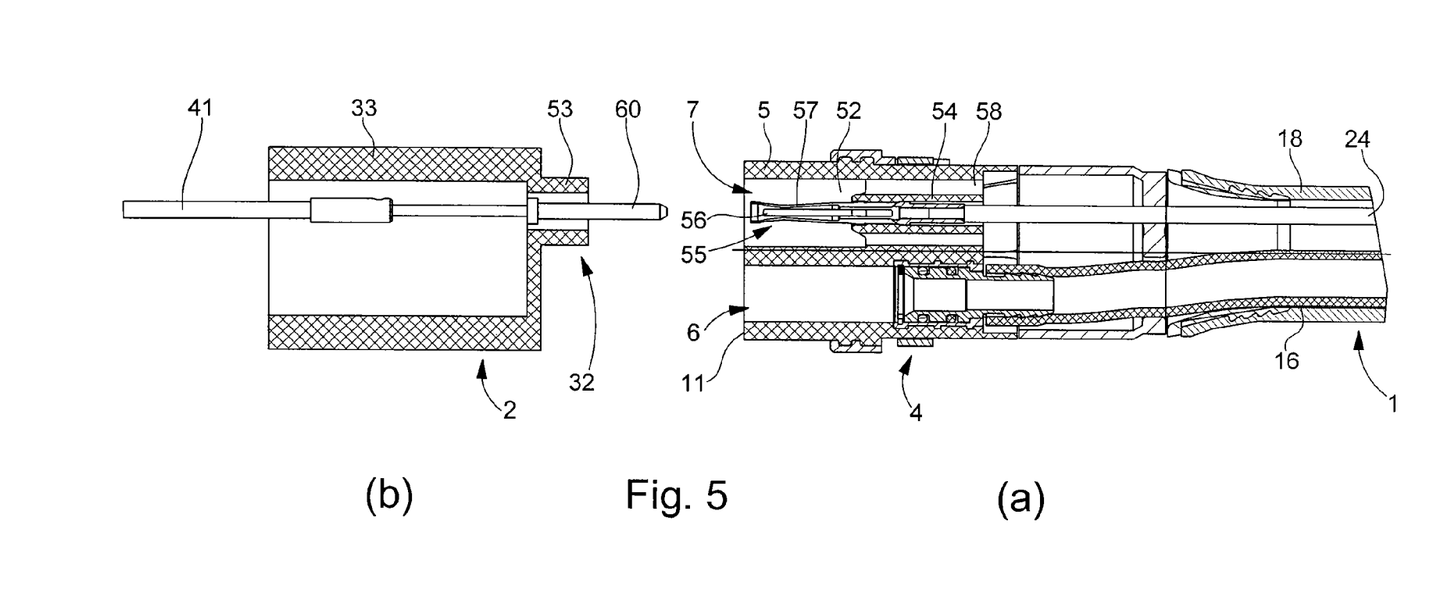
FIG. 5 is a view similar to FIG. 3 and shows in a schematic manner a fourth embodiment showing a female coupling at (a) and a male coupling at (b).

FIG. 5 shows partially and schematically a variant of the construction of FIG. 2, that differs in the arrangement of the electric contact members. Moreover, in this example, the return air tube 17 of FIG. 2 is omitted, since supply pipe 1 is provided in this case for instruments that do not need a return air conduit, in particular handpieces with an electric motor. However, these handpieces may need an additional electric line for transmitting measurement or control signals, for example a signal indicating the couple generated by the motor, or for transmitting a current in order to power the motor or another member. This line is formed by the additional conductors 24 and 41 described in the preceding examples and connected to each other by the female conductor 7 and male conductor 32.

Female conductor 7 comprises a cylindrical bore 52 arranged in insulating body 5 and into which a cylindrical end portion 53 of male connector 2 is fitted. Inside bore 52, body 5 includes a recessed support 54 carrying at the centre of bore 52 a metal contact sleeve 55, the front part of which is provided with slots 56 delimiting resilient strips 57. The recessed support 54 comprises channels 58 for the passage of air, if necessary. The front end of sleeve 55 is preferably set back from front face 11 of the insulating body. The end of conductor 24 is stripped of its insulating sheath and fixed in the back part of sleeve 55. If there is no return air tube in supply pipe 1, conductor 24 is simply housed inside the sheath 18 of the pipe, or it can be grouped with the other electric lines.

In male connector 32, conductor 41 is coupled to a contact pin 60 carried by an element that is not shown of insulating body 33 of coupling 2. This pin is at the centre of the conduit formed by end portion 53 and, when the two couplings 2 and 4 are coupled, it is plugged into sleeve 55 to ensure the electrical connection between conductors 24 and 41.

Of course, the electric pin and sleeve connection system shown in FIG. 5 could also be integrated in return air conduit 13 shown in FIG. 2 and formed by tubes 17 and 42, or to another of the dual function connectors of couplings 2 and 4 described hereinbefore.

The invention claimed is:

1. A supply pipe for connecting an instrument for dental or surgical use to a control and supply unit, said supply pipe comprising:
   (a) a plurality of fluid conduits and a plurality of electric lines; and
   (b) at a front end, a universal coupling for connecting different types of said instrument in a removable manner to part or all of the plurality of fluid conduits and the plurality of electric lines, wherein the universal coupling includes a plurality of fluid connectors coupled to the plurality of fluid conduits and a plurality of electric connectors coupled to the plurality of electric lines, wherein each fluid connector of the plurality of fluid connectors and each electric connector of the plurality of electric connectors occupies a place on a front face of the universal coupling;
   (c) an insulating body made of insulating synthetic material; and
   (d) at least one dual fluidic and electric function connector, wherein the at least one dual function connector is one of the plurality of fluid connectors of the universal coupling, and the at least one dual function connector includes at least one additional electric line including an additional conductor that is not coupled to one of the plurality of electric connectors, wherein the additional conductor is coupled to the at least one dual function connector, and the at least one dual function connector extends into the insulating body in the supply pipe and is arranged to provide a choice between a fluid connection, an electric connection, or both the fluid connection and the electric connection.

2. The supply pipe according to claim 1, wherein the dual function connector includes a metal first tubular part electrically connected to the additional conductor and coupled to a flexible second tube extending into the pipe to form, with said flexible second tube, a fluid conduit, wherein said metal first tubular part forms both an electric contact member and a fit member for cooperating with a third tubular part, wherein said third tubular part is part of an instrument connector connected to said instrument.

3. The supply pipe according to claim 2, wherein the additional conductor is arranged in a wall of said flexible second tube.

4. The supply pipe according to claim 3, wherein the conduit associated with the dual function connector is an air conduit.

5. The supply pipe according to claim 2, wherein the additional conductor is arranged outside said flexible second tube.

6. The supply pipe according to claim 5, wherein the conduit associated with the dual function connector is an air conduit.

7. The supply pipe according to claim 2, wherein the conduit associated with the dual function connector is an air conduit.

8. The supply pipe according to claim 2, wherein the additional conductor is arranged in the fluid conduit inside said flexible second tube.

9. The supply pipe according to claim 8, wherein the additional conductor is coupled to a metal sleeve secured to said metal first tubular part and located in the fluid conduit.

10. The supply pipe according to claim 9, wherein the conduit associated with the dual function connector is an air conduit.

11. The supply pipe according to claim 8, wherein the conduit associated with the dual function connector is an air conduit.

12. The supply pipe according to claim 1, wherein the conduit associated with the dual function connector is an air conduit.

13. The supply pipe according to claim 1, wherein the dual function connector includes a cylindrical bore arranged in the insulating body of the universal coupling, and a contact element arranged at the center of said cylindrical bore and electrically connected to the additional conductor.

14. A supply pipe for connecting an instrument for dental or surgical use to a control and supply unit, said supply pipe comprising:
   (a) a plurality of fluid conduits and a plurality of electric lines; and
   (b) at a front end, a universal coupling for connecting different types of said instrument in a removable manner to part or all of the plurality of fluid conduits and the plurality of electric lines, wherein the universal coupling includes a plurality of fluid connectors coupled to the plurality of fluid conduits and a plurality of electric connectors coupled to the plurality of electric lines, wherein each fluid connector of the plurality of fluid connectors and each electric connector of the plurality of electric connectors occupies a place on a front face of the universal coupling; and
   (c) at least one dual fluidic and electric function connector, wherein the at least one dual function connector is one of the plurality of fluid connectors of the universal coupling, and the at least one dual function connector includes at least one additional electric line including an additional conductor that is not coupled to one of the plurality of electric connectors, wherein the additional conductor extends freely inside the at least one dual function connector, and the at least one dual function connector extends into the supply pipe and is arranged to provide a choice between a fluid connection, an electric connection, or both the fluid connection and the electric connection.

15. A supply pipe for connecting an instrument for dental or surgical use to a control and supply unit, said supply pipe comprising:

(a) a plurality of fluid conduits and a plurality of electric lines;
(b) at a front end, a universal coupling for connecting different types of said instrument in a removable manner to part or all of the plurality of fluid conduits and the plurality of electric lines, wherein the universal coupling includes a plurality of fluid connectors coupled to the plurality of fluid conduits and a plurality of electric connectors coupled to the plurality of electric lines, wherein each fluid connector of the plurality of fluid connectors and each electric connector of the plurality of electric connectors occupy a place on a front face of the universal coupling;
(c) an insulating body made of insulating synthetic material; and
(d) at least one dual fluidic and electric function connector connected to a first fluid conduit of the plurality of fluid conduits, wherein the dual function connector is one of the plurality of fluid connectors of the universal coupling, and the at least one dual function connector includes at least one additional electric line including an additional conductor that is not coupled to one of the plurality of electric connectors, wherein the additional conductor is coupled to the at least one dual function connector, and the at least one dual function connector extends into the insulating body in the supply pipe and is arranged to provide a choice between a fluid connection, an electric connection, or both the fluid connection and the electric connection, and wherein the additional conductor is a flexible conductor extending freely inside the first fluid conduit.

16. The supply pipe according to claim 15, wherein the additional conductor is an earth line.

17. The supply pipe according to claim 16, wherein the additional conductor is a non-insulated copper braid wire.

18. The supply pipe according to claim 16, wherein the first fluid conduit is a return air tube.

19. The supply pipe according to claim 15, wherein the additional conductor is an insulated conductor and either the additional conductor is not an earth line or the first fluid conduit contains a conductive fluid.

* * * * *